US009295848B2

(12) United States Patent
Meskens (10) Patent No.: US 9,295,848 B2
(45) Date of Patent: Mar. 29, 2016

(54) ANTENNA FOR BEHIND-THE-EAR (BTE) DEVICES

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 239 days.

(21) Appl. No.: 12/935,277

(22) PCT Filed: Mar. 26, 2009

(86) PCT No.: PCT/AU2009/000352
§ 371 (c)(1),
(2), (4) Date: Sep. 28, 2010

(87) PCT Pub. No.: WO2009/117778
PCT Pub. Date: Oct. 1, 2009

(65) Prior Publication Data
US 2011/0022121 A1    Jan. 27, 2011

(30) Foreign Application Priority Data
Mar. 28, 2008 (AU) ................. 2008901474

(51) Int. Cl.
*A61N 1/08* (2006.01)
*A61N 1/372* (2006.01)
*A61N 1/375* (2006.01)
*H04R 25/00* (2006.01)

(52) U.S. Cl.
CPC ............ *A61N 1/37229* (2013.01); *A61N 1/375* (2013.01); *H04R 25/606* (2013.01); *H04R 2225/51* (2013.01); *H04R 2225/63* (2013.01)

(58) Field of Classification Search
CPC .......... A61N 1/37229; A61N 1/37211; H04B 5/0031; H04B 5/0081; H02J 7/025
USPC ....................................... 607/55–57
See application file for complete search history.

(56) References Cited

U.S. PATENT DOCUMENTS

| | | | |
|---|---|---|---|
| 5,606,621 A | 2/1997 | Reiter et al. | |
| 6,067,474 A * | 5/2000 | Schulman et al. | 607/57 |
| 6,748,094 B1 | 6/2004 | Tziviskos et al. | |
| 7,020,298 B1 | 3/2006 | Tziviskos et al. | |
| 7,142,926 B2 | 11/2006 | Crawford | |
| 2004/0073275 A1* | 4/2004 | Maltan et al. | 607/57 |
| 2006/0184212 A1* | 8/2006 | Faltys et al. | 607/57 |
| 2006/0243811 A1* | 11/2006 | Koyama et al. | 235/492 |
| 2007/0288066 A1* | 12/2007 | Christman et al. | 607/60 |
| 2008/0119138 A1* | 5/2008 | Kim et al. | 455/41.2 |

(Continued)

FOREIGN PATENT DOCUMENTS

| | | |
|---|---|---|
| KR | 100781228 | 11/2007 |
| WO | WO-03/076012 | 9/2003 |

OTHER PUBLICATIONS

European Application No. 09725199.5, Extended European Search Report mailed on Feb. 18, 2011, 5 Pages.

(Continued)

*Primary Examiner* — Michael Kahelin
*Assistant Examiner* — Minh Duc Pham (57) ABSTRACT

An improved antenna device for BTE devices, such a hearing prostheses, is disclosed. Antenna elements (111, 114) are disposed in the BTE body (101) and in the earhook (102), with dielectric material (112, 113) disposed between, so as to form a capacitive coupling.

20 Claims, 6 Drawing Sheets (56) References Cited

U.S. PATENT DOCUMENTS

2008/0300658 A1    12/2008    Meskens
2008/0304686 A1    12/2008    Meskens et al.
2009/0228074 A1*    9/2009    Edgell et al. .................. 607/60
2009/0270948 A1*   10/2009    Nghiem et al. ................ 607/60

OTHER PUBLICATIONS

European Application No. 09725199.5, Supplementary European Search Report mailed on Mar. 8, 2011, 1 Page.
International Search Report for PCT/AU2009/000352, filed Mar. 26, 2009, mailed May 12, 2009.

* cited by examiner

ANTENNA FOR BEHIND-THE-EAR (BTE) DEVICES

CROSS-REFERENCE TO RELATED APPLICATION

The present application is a National Stage application of PCT/AU2009/000352 entitled "Antenna For Behind-The-Ear (BTE) Devices", filed on Mar. 26, 2009, which claims priority from Australian Provisional Patent Application No. 2008901474, filed on Mar. 28, 2008, which are hereby incorporated by reference herein.

BACKGROUND

1. Field of the Invention

The present invention relates generally to Behind-the-Ear (BTE) devices that wirelessly communicate with implantable hearing aid system prostheses, and more particularly to a radio frequency antenna for a BTE device.

2. Related Art

Implantable hearing prostheses, such as cochlear implants, typically include an internal portion with a receiver and electrical stimulator secured in bone beneath the skin, and an external BTE device with a microphone, speech processor and an antenna.

The antenna is used for communicating processed sound information over a radio frequency link to the implant, communication with a remote control device for the hearing aid or implant, or in some cases for bilateral communication between two or more BTE devices. The radio frequency antenna is also used to provide a convenient transcutaneous link.

Typically, the radio frequency antenna is implemented entirely inside the body of the BTE device, with much effort taken to optimise the antenna efficiencies so as to improve the wireless link performance and range. As a consequence, however, the size of the BTE devices are governed by the size of antenna implemented within the body of the BTE.

It is desirable for BTE devices to be smaller and as a consequence, the current trend is for some BTE devices to be constructed with a part of the antenna implementation inside earhook portions of the BTE device. However, these earhook antennas are often connected to the antenna connector on the BTE device using an inefficient and unreliable electrical galvanic connection, particularly in higher radio frequency ranges.

U.S. Pat. No. 6,748,094 to Advanced Bionics Corporation discloses a connector system for detachably connecting earhooks to a BTE device, based upon galvanic connections between the earhook and BTE device.

SUMMARY

In a first aspect of the invention, there is provided a BTE device for transmitting and/or receiving information via radio frequency, said BTE device comprising: a body portion including a first antenna element fitted in the body portion of the BTE device; and an earhook including a second antenna element fitted in the earhook, wherein said first and second antenna elements are electrically coupled together by a capacitive connection so that one antenna element is able to extend the operation of the other antenna element.

In a second aspect, there is provided a BTE device for transmitting and/or receiving information via radio frequency, said BTE device comprising: a first antenna element fitted in a body portion of the BTE device; and a second antenna element fitted in an earhook adapted to be attached to the BTE device, wherein the first antenna element is adapted to be electrically coupled to the second antenna element; and wherein said first and second antenna elements are electrically coupled by a capacitive connection so that one antenna element is able to extend the operation of the other antenna element.

In a third aspect, there is provided an earhook adapted to be attached to a body portion of a BTE device for transmitting and/or receiving information via radio frequency, said earhook comprising: a first antenna element fitted in the earhook; and adapted to be electrically coupled to a second antenna element fitted in the body portion of the BTE device, wherein said first and second antenna elements are electrically coupled by a capacitive connection so that one antenna element is able to extend the operation of the other antenna element.

BRIEF DESCRIPTION OF THE DRAWINGS

Illustrative implementations of the present invention will be described with reference to the accompanying figures, in which:

FIG. 1b is a schematic view of the earhook and a section of the BTE body of the implementation shown in FIG. 1a.

FIG. 2 is a schematic view illustrating an alternative construction of the antenna element in the earhook of the implementation shown in FIG. 1a;

DETAILED DESCRIPTION

Aspects of the present invention are generally directed to providing a Behind the Ear (BTE) device with an antenna arrangement that is partly inside the body of the BTE device and partly inside the earhook, with the two antenna elements being electrically coupled by a capacitive connection. In this way, the antenna elements are able to operate as a single antenna.

As part of the antenna is provided in the earhook as well as in the body of the BTE device, this arrangement allows the body of the BTE device to be reduced in size, while a reliable connection is retained between the two antenna elements using a capacitor based coupling. Such a coupling provides a more efficient and reliable electrical connection than the galvanic connections provided in the prior art, especially in the higher radio frequency ranges, i.e. upwards of about 400 MHz.

Aspects of the present invention are applicable to a wide variety of BTE devices, and allow an antenna element in the body of a BTE device to be reliably coupled to an antenna element in an earhook that is attached to, or can be attached to the BTE device. These aspects may be applied to any BTE device that includes an antenna, for example hearing prostheses such as cochlear implants and hearing aids. These aspects may also be applied to BTE devices that do not perform a medical function.

The BTE device may be adapted to transmit information to and/or receive information from an implant, for example, the neurological stimulator of a cochlear implant. Alternatively, or in addition, the BTE device may be adapted to transmit information to and/or receive information from one or more other BTE devices, allowing bilateral communication between the BTE devices. It may be used to provide communication with other external or implanted devices via RF communications, for example, remote control units or other sound sources.

Whilst aspects of the invention will be mainly explained with reference to a BTE device for use within an implantable cochlear implant system, it will be appreciated that this is illustrative, and in no way limits the applicability of the present invention.

Figure 1A:
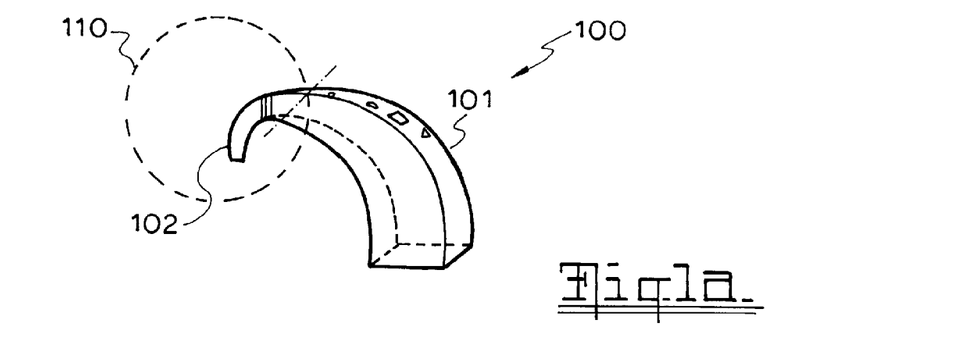
FIG. 1a is a perspective view of a BTE device consisting of a BTE body and an attached earhook, in accordance with one implementation of the present invention.

Referring firstly to FIG. 1a, a BTE device 100 consisting of a BTE body 101 and an attached earhook 102 is shown. It is preferred that the electromagnetic antenna system 110 is located on the upper part of the BTE device 100, although alternative constructions are envisioned.

Figure 1B:
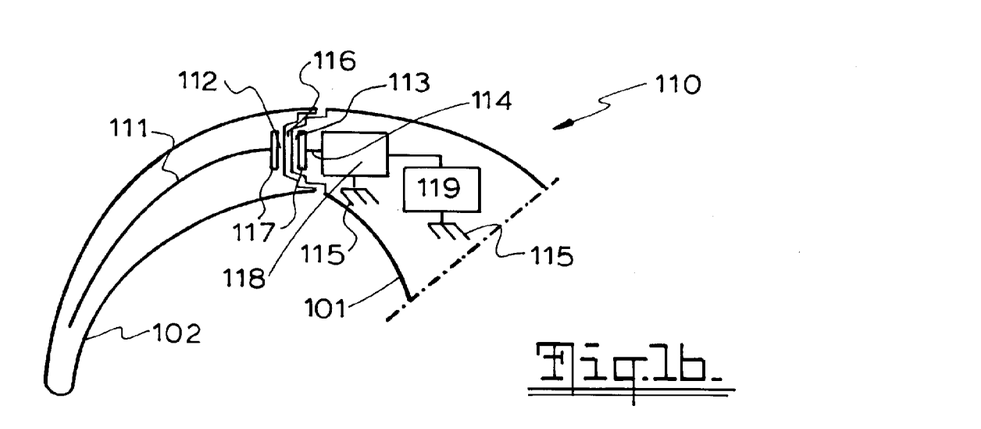

Referring now to FIG. 1b, the antenna system 110 includes a number of parts:

an earhook 102, which is made of an electrical non-conductive material or isolator;—a first antenna element 111 in the earhook 102, consisting of an electrical conductive part (e.g. wire);

a first dielectric material 112 ($\in_{r1}$), which could be made of the same material as the earhook 102;

a second dielectric material 113 ($\in_{r2}$), which could be made of the same material as the enclosure of the BTE device 101;

a second antenna element 114 in the body of the BTE device 101, consisting of an electrical conductive part (e.g. wire);

a matching unit (optional) 118;

a receiver and/or transmitter 119; and an antenna groundplane 115 (monopole antenna), which may be the ground layer of the PCB board located in the body of the BTE device 101, or a second antenna pole element (dipole antenna) in the body of the BTE 101.

It is to be understood that the feeder point of the second antenna element 114 is able to be connected by a PCB track, preferably using a strip-line or a second pole element (dipole antenna) in the body of the BTE 101 (not shown) with a characteristic impedance of between 30 and 100 Ohms.

The earhook 102 is mechanically firmly attached to the body of the BTE device 101 and may be configured for mechanical detachment, allowing the earhook 102 to be easily replaced should the earhook antenna element 111 malfunction, or if an alternative earhook is desired. While it is possible for an air-gap 116 ($\in_{ro}$=1) to exist between the earhook 102 and the body of the BTE device 101, it is desirable that such an air-gap 116 be minimized to obtain a most efficient coupling of the two antenna elements.

The electrical conductive materials within the BTE device 100 are separated from each other by dielectric material. The BTE shell device is often formed by hard and rigid polymer material such as polymerized acrylates or medical grade hypoallergenic plastic shell materials with nano coating. The earhook is made of softer polymer materials such as flexible polyvinyl chloride or flexible silicon rubbers.

Figure 4:
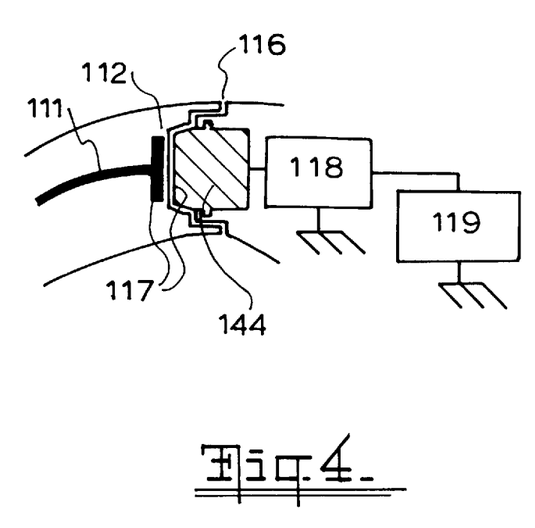
FIG. 4 is a schematic view illustrating an alternative implementation of the present invention in which the second dielectric material is absent.

It will be appreciated that the dielectric is not necessarily required to be formed of plastic materials or silicon rubbers from which respectively the BTE enclosure 101 or earhook 102 could be formed. Examples of other dielectric materials may include ceramic materials or polytetrafluoroethylene (PTFE/Teflon™). In fact, the dielectric can be a thin film, layer, or durable coating placed upon the conductive material. Examples of coatings may include PTFE coatings, crystal clear film coatings, metal oxides (such as barium titanium oxide), and ceramic coatings. Furthermore, alternative constructions may be provided in which the first dielectric material 112 or second dielectric material 113 is absent or removed. FIG. 4 illustrates an embodiment where the second dielectric material is absent. The second antenna element 144 could be for example a bolt or a press-stud.

Embedding a part of the antenna in the earhook 102 not only results in a simpler production process for the body portion of the BTE device 101, but also improves the overall antenna efficiency/gain. By utilizing the full physical length of the antenna for obtaining resonance, e.g. $\lambda/4$, $5\lambda/8$, the effective antenna height and/or antenna conversion factors improve. While a physically shorter antenna could also be placed in resonance by adding an inductance in series with the feeder line, effectively replacing the missing antenna length in order to obtain $\lambda/4$, such an arrangement decreases the overall efficiency of the antenna arrangement.

The first and/or second antenna elements 111, 114 may be fitted entirely within the earhook 102 and the body portion of the BTE device 101 respectively, advantageously providing additional protection to the antenna elements 111, 114 and allowing the body portion of the BTE device 101 and/or the earhook 102 to be more aesthetically pleasing.

The operation of the electrical connection provided by the capacitor coupling of the capacitor plates 117 will now be described.

Figure 1C:
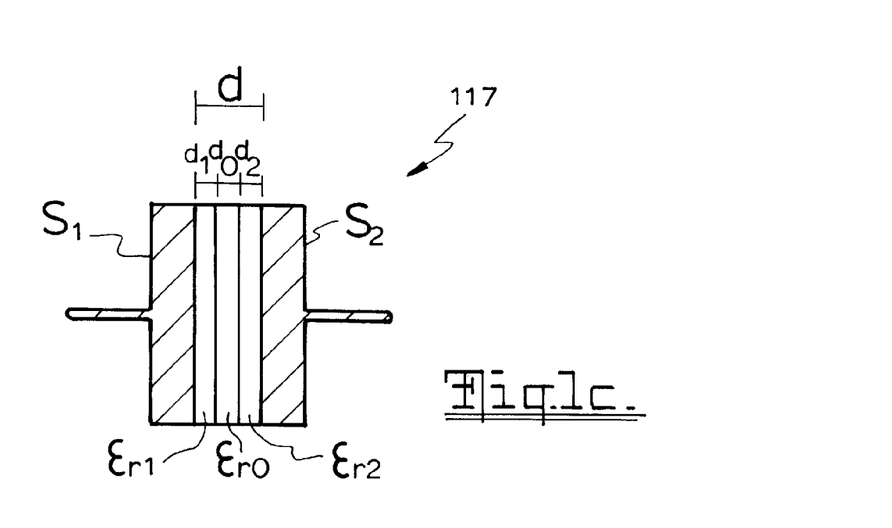
FIG. 1c is a schematic view of the capacitive connection of the implementation shown in FIG. 1b.

Referring now to FIG. 1c, the surfaces of both conductive parts facing each other may be considered as plates 117 of a capacitor, with a distance 'd' separating the plates. The capacitance is proportional to the surface area of the conducting plate 'S' ($S=S_1=S_2$) and inversely proportional to the distance 'd' between the plates. It is also proportional to the permittivity ($\in_s$) of the dielectric that separates the plates. The capacitance value 'C of a parallel-plate capacitor, expressed in 'Farad', is given by:

$$C = \varepsilon_s \frac{S}{d} \text{ with } A \gg d^2 \quad \text{[Equation 1]}$$

where:

S is the area of the plates in square meters, and d is the spacing of the plates, expressed in meters;

$\in_s = \in_0 \in_r$ is the static permittivity of the insulator:

$\in_0$ is the constant for the permittivity of free space (8.85×10-12); and $\in_r$ is the relative static permittivity or dielectric constant of the material between the plates.

The dielectric of the capacitor may be any material residing between the two conductive plates. It could be a combination of a maximum of three different types of stacked dielectric materials: $\in_{r1}$, $\in_{r0}$ and $\in_{r2}$.

Each dielectric of the stack can be represented as an individual capacitor in series ($C_{S1}$, $C_{S0}$, $C_{S2}$):

$$C = \cfrac{1}{\cfrac{1}{C_{S1}} + \cfrac{1}{C_{S0}} + \cfrac{1}{C_{S2}}} = \cfrac{1}{\cfrac{d_1}{\varepsilon_0 \cdot \varepsilon_{r0} \cdot S} + \cfrac{d_0}{\varepsilon_0 \cdot \varepsilon_{r0} \cdot S} + \cfrac{d_2}{\varepsilon_0 \cdot \varepsilon_{r0} \cdot S}} \quad \text{[Equation 2]}$$

'Equation 3' gives the real part of the impedance of a capacitor in function of frequency:

$$X_c = |Z| = \left| \frac{1}{j \cdot 2\pi f \cdot C} \right| = \frac{1}{2\pi f C} X_C \quad \text{[Equation 3]}$$

where:
'f' the frequency, expressed in 'Hz';
C the capacitance, expressed in 'Farad'; and
$X_c$ is the capacitive reactance expressed in 'Ohm'.

To achieve reliable coupling between the first and second antenna elements, it is desirable to obtain a low capacitive reactance ($X_c \approx 0$). This is done by:
decreasing 'd' as much as possible; and
increasing 'S' and $\in_r$ as much as possible.

From 'Equation 3', it will be understood that it is also advantageous to operate at high frequencies, for example 2.4 GHz.

The total length of the antenna system is mostly determined by the operation frequency. Accordingly, to obtain good efficiency, it is desirable to place the antenna in resonance, resulting in no imaginary impedance part. Otherwise, the antenna impedance is required to be complex and conjugated to its source impedance.

To compensate for any residual $X_c$ on the antenna, a series inductance XL (reactive inductance), for example, may be added. This can be achieved by a matching circuit or increasing the length of one of the antenna elements.

It is preferred that the length of the electrical conductive parts of the antenna equal to $\lambda/4$ in order to obtain antenna resonance (purely resistive impedance) at the operating frequency, eg:

$$\text{antenna length in free space} = \frac{\lambda}{4} = \frac{1}{4} \cdot \frac{c}{f} = \frac{300000 \text{ km/s}}{4 \times 2.4 \text{ GHz}} = 31.25 \text{ mm/}\Lambda$$

For a mixed human tissue/air environment, the physical antenna length will decrease (typically by a factor of 2 for BTE devices), ie:

$$\text{antenna length} = \frac{\text{antenna length in free space}}{\sqrt{\varepsilon_{avg,environment}}}$$

Figure 2:
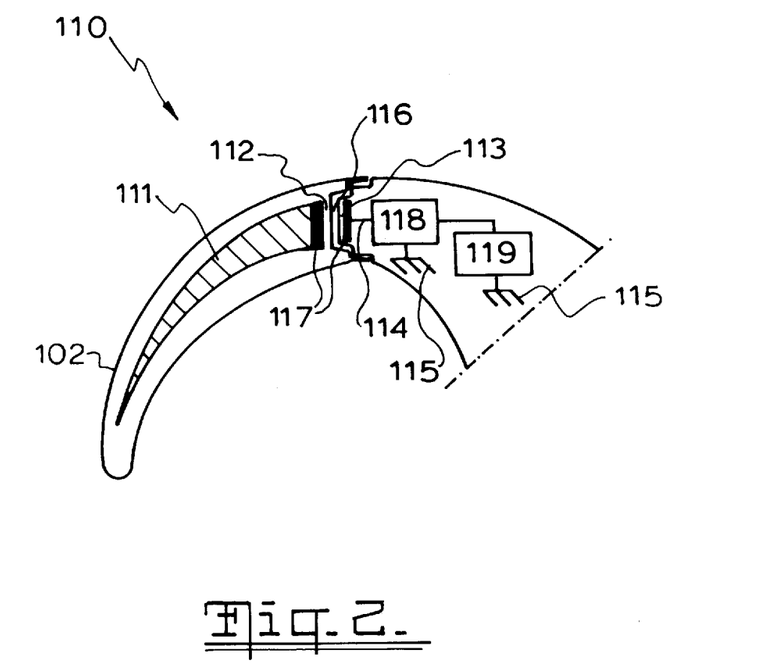

Referring to FIG. 2, the conductive antenna elements 111, 114 may have different geometric shapes as required to suit the earhook 102 and/or the wearer, for example, a bended cone shape for the first antenna element 111.

Figure 3A:
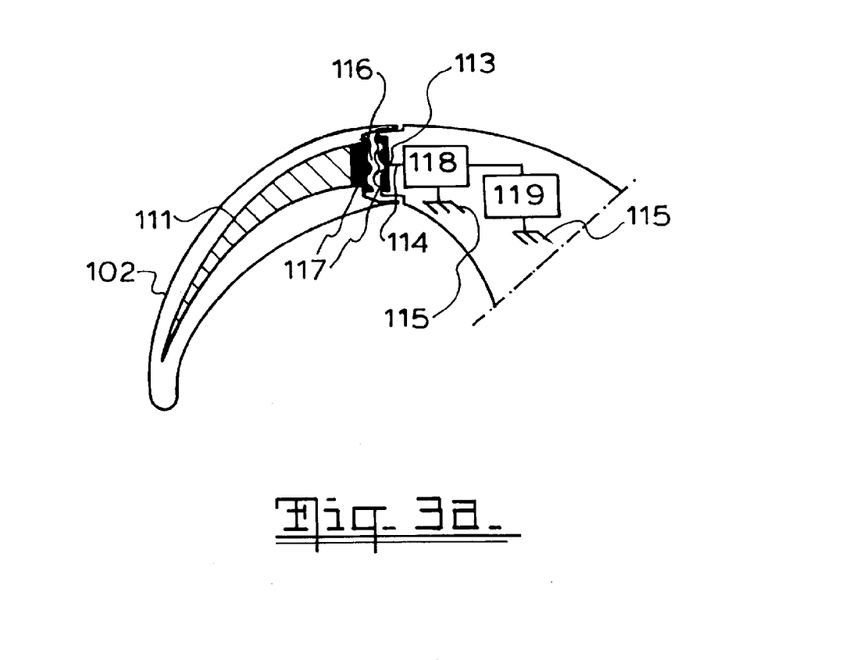
FIGS. 3a and 3b are schematic views illustrating alternative configurations of the capacitor plates of the implementation shown in FIG. 2.
Figure 3B:
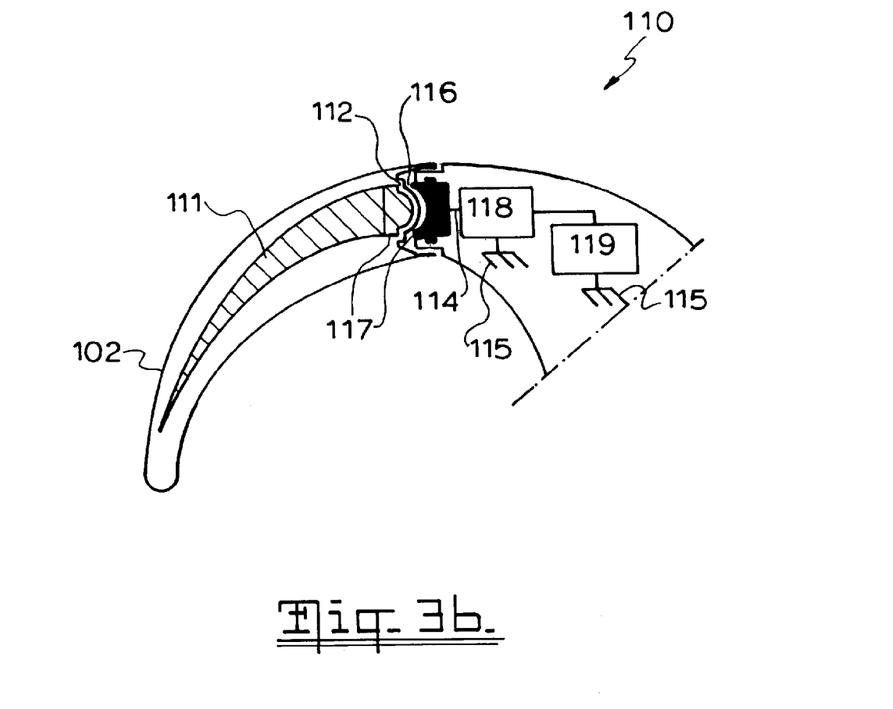

Referring to FIGS. 3a and 3b, in an alternative implementation, one of the first or second antenna elements 111, 114 may be formed with a projecting portion at one end that is adapted to co-operate with a projection receiving portion formed at one end of the other of the first or second antenna elements 111, 114. Such configurations advantageously allow the surface area of capacitor plates 117 of the first and second antenna elements 111, 114 to be maximised, resulting in a more efficient and reliable capacitive connection between the elements.

Accordingly, the surface areas of the capacitor plates 117 can be increased in size by using curved surfaces on each of the capacitor plates. It will be appreciated that other surface increasing configuration such as cooperating triangular shapes on surface each of the capacitor plates 117 may also be used. Such configurations provide a higher capacitance and allow a more reliable coupling to be obtained, without the need for the diameter of the earhook 102 to be increased.

Figure 5A:
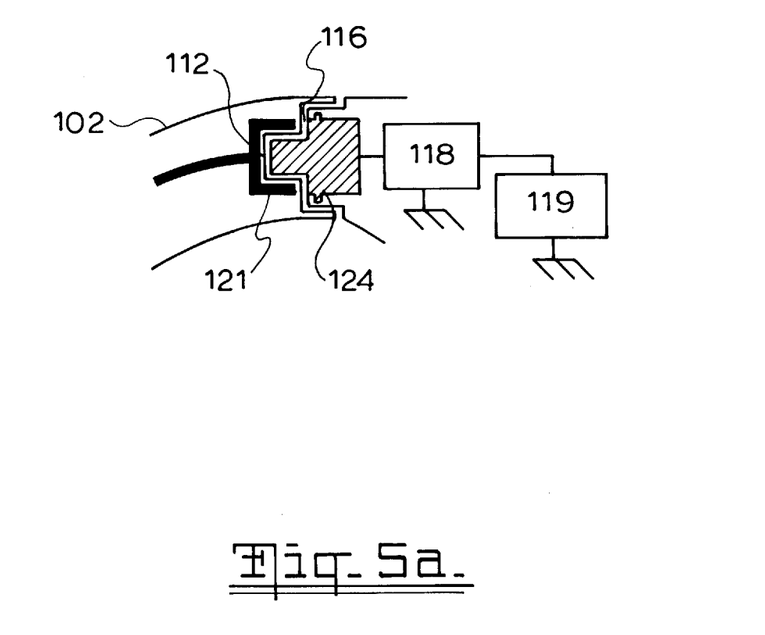
FIGS. 5a and 5b are schematic views illustrating alternative constructions of the conductive elements of an alternative implementation of the present invention.
Figure 5B:
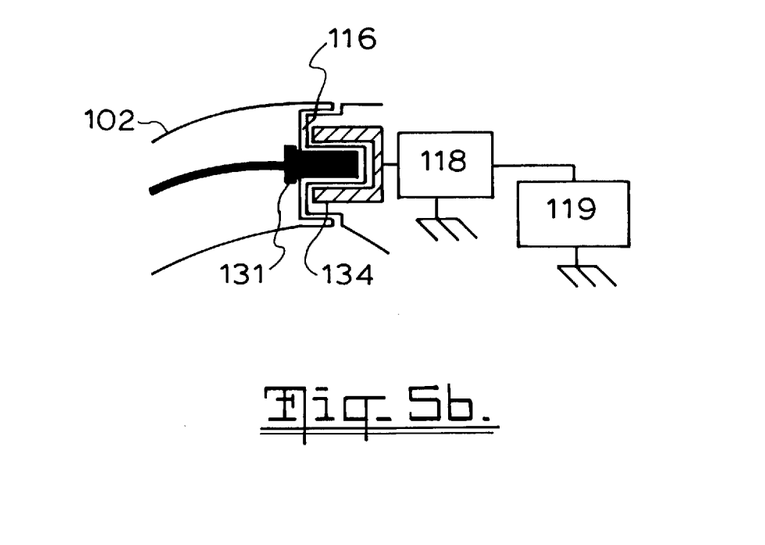

Referring to FIG. 5a, in an alternative implementation, the capacitor may be formed by a cylindrical conductive hollow element 121 inside the earhook 102, capacitively coupled to the second cylindrical antenna element 124 in the body of the BTE device. Alternatively, as illustrated in FIG. 5b, the capacitor may be formed by a cylindrical conductive hollow element inside the body of the BTE device, capacitively coupled to the cylindrical antenna element 131 inside the earhook 102.

Figure 6:
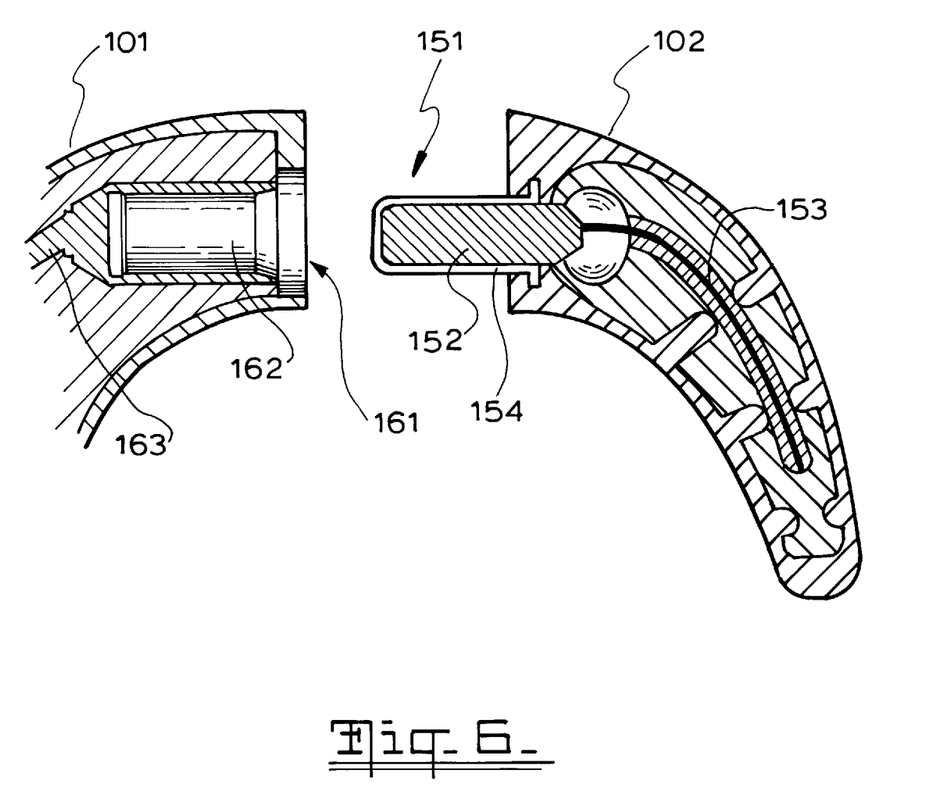
FIG. 6 is a cross-sectional view of one implementation of the present invention.

One implementation of the present invention, illustrated in FIG. 6 includes an earhook 102 with an insulated projection 151 formed at one face and adapted to be fitted into a conductive receptacle portion 161 on the respective face of a BTE device 101.

The projection 151 of the earhook includes a conductive insert 152 surrounded by insulating material 154 ($\in_{r1}$). The conductive insert 152 is connected to a conductive wire 153 provided within a channel formed in the earhook 102, thereby forming a first antenna element.

The receptacle 161 in the body of the BTE device 101 is in the form of a hollow cylinder 162 of a size suitable to fit the projection 151 of the earhook, and is connected to the PCB track 163 in the body of the BTE device 101, thereby forming a second antenna element.

Once the projection 151 of the earhook 102 is inserted into the receptacle 161 in the body of the BTE device 101, the first and second antenna elements are electrically coupled together by a capacitive connection, effectively forming a single antenna. This implementation allows for a larger surface area S and a lower capacitive reactance may be obtained.

The implementation shown in FIG. 6 may be configured with the following dimensions to operate at 2.40 GHz.
The conductive wire 153 having a length of 11 mm, provided within the earhook 102 of approximately 17 mm in length.
The conductive insert 152 having diameter of 2.2 mm and a length of 4.6 mm, surrounded by the insulating material 154 of approximately 0.2 mm thickness.
The hollow cylinder 162 having a diameter of 2.7 mm and a depth of 5.5 mm for receiving the conductive insert 152.

It will be appreciated that the above dimensions show one possible implementation and accordingly do not limit alternative implementations of the invention.

It will also be appreciated that aspects of the invention may be applied to all kinds of BTE devices that operate using wireless electromagnetic links, for example:
Wireless electromagnetic analogue or digital modulated RF links in the VHF or UHF bands; and
Bluetooth™ and ultra low power wireless devices worn behind-the-ear, headsets, etc.

It will be appreciated that there are many possible implementations of the present invention, and that variations and additions are possible within the general inventive concept. Many structural and functional equivalents are available, as will be apparent to those skilled in the art.

The invention claimed is:

1. A behind-the-ear (BTE) device configured to transmit and/or receive information via radio frequency, the BTE device comprising:
a body portion including:
a first capacitor plate,
a first antenna element fitted in the body portion of the BTE device, wherein the first antenna element has a first end and a second end, and wherein the second end of the first antenna element is electrically connected to the first capacitor plate; and
an earhook portion configured to be mechanically coupled to the body portion and including:
a second capacitor plate,
a second antenna element fitted in the earhook portion, wherein the second antenna element has a first end and a second end, and wherein the first end of the second antenna element is electrically connected to the second capacitor plate,
wherein the first and second capacitor plates are positioned such that, when the earhook portion is mechanically coupled to the body portion, the first and second capacitor plates electrically couple the first and second antenna elements together so that the first and second antenna elements are able to operate as a single antenna.

2. The BTE device of claim 1, wherein the BTE device is further configured to transmit information to and/or receive information from an implant.

3. The BTE device of claim 1, wherein the BTE device is further configured to transmit information to and/or receive information from one or more other BTE devices.

4. The BTE device of claim 1, wherein one of the first or second capacitor plates is formed with at least one projecting portion which is adapted to co-operate with at least one projection receiving portion formed at the other of the first or second capacitor plates.

5. The BTE device of claim 4, wherein the first and second capacitor plates comprise complimentary curved shapes.

6. The BTE device of claim 4, wherein the first capacitor plate has a cylindrical shape and the second capacitor plate has a hollow cylindrical shape so as to be disposed around the first capacitor plate having the cylindrical shape.

7. The BTE device of claim 4, wherein the second capacitor plate has a cylindrical shape and the first capacitor plate has a hollow cylindrical shape so as to be disposed around the second capacitor plate having the cylindrical shape.

8. The BTE device of claim 7, wherein the earhook includes an elongate insulated projection in which the second capacitor plate having the cylindrical shape is disposed, and wherein the body portion includes an elongate receptacle configured to receive and mate with the insulated projection, and wherein the first capacitor having the hollow cylindrical shape is disposed around the elongate receptacle.

9. An earhook adapted to be removably attached to a body portion of a behind-the-ear device, the earhook comprising:
a second antenna element disposed in the earhook; and
a second capacitor plate electrically connected to the second antenna element, wherein the second capacitor is configured to be capacitively coupled to a first capacitor plate electrically connected to a first antenna element disposed in the body portion of the BTE device so that the first and second antenna elements are able to operate as a single antenna.

10. The earhook of claim 9, wherein the second capacitor plate is formed with at least one projecting portion which is adapted to co-operate with at least one projection receiving portion formed in the first capacitor plate.

11. The earhook of claim 10, wherein the first capacitor plate has a hollow cylindrical shape, and wherein the second capacitor plate has a cylindrical shape configured to be positioned inside the first capacitor plate having the hollow cylindrical shape.

12. The earhook of claim 11, further comprising:
an elongate insulated projection in which the second capacitor plate having the cylindrical shape is disposed, and wherein the body portion includes an elongate receptacle configured to receive and mate with the insulated projection, and wherein the first capacitor having the hollow cylindrical shape is disposed around the elongate receptacle.

13. The earhook of claim 9, wherein the second capacitor plate is formed with at least one projection receiving portion which is adapted to co-operate with at least one projection portion formed in the first capacitor plate.

14. The earhook of claim 13, the first capacitor plate has a cylindrical shape, and wherein the second capacitor plate has a hollow cylindrical shape so as to be disposed around the first capacitor plate having the cylindrical shape.

15. The earhook of claim 9, wherein the second capacitor plate has a curved shape that is complimentary to a curved shape of the first capacitor plate.

16. A behind-the-ear device, comprising:
a body portion in which a transmitter unit, a first capacitor plate, and a first antenna element are disposed, wherein the first antenna element is electrically connected between the transmitter unit and the first capacitor plate; and
an earhook portion in which a second capacitor plate and a second antenna element are disposed, wherein the second antenna element is electrically connected to the second capacitor plate,
wherein the first and second capacitor plates are configured to be electrically coupled to each other to enable the first and second antenna elements to operate as a single antenna for transmission of radio frequency signals by the transmitter unit.

17. The behind-the-ear device of claim 16, wherein the transmitter unit is also a receiver unit, and wherein when the first and second antenna elements enable the transmitter unit to transmit information to and/or receive information from an implant.

18. The behind-the-ear device of claim 16, wherein the transmitter unit is also a receiver unit, and wherein when the first and second antenna elements enable the transmitter unit to transmit information to and/or receive information from one or more other behind-the-ear device devices.

19. The behind-the-ear device of claim 16, wherein one of the first or second capacitor plates is formed with at least one projecting portion which is adapted to co-operate with at least one projection receiving portion formed at the other of the first or second capacitor plates.

20. The behind-the-ear device of claim 19, wherein the first and second capacitor plates comprise cooperating curved shapes.

* * * * *